US008920793B2

(12) United States Patent
Lee et al.

(10) Patent No.: US 8,920,793 B2
(45) Date of Patent: Dec. 30, 2014

(54) BIODEGRADABLE PAOX POLYMER PARTICLE WITH CATIONIC PROPERTY

(75) Inventors: Dong Won Lee, Jeonbuk (KR); Kyeong Yeol Seong, Jeonbuk (KR); Han Sol Seo, Jeonbuk (KR); Hyung Min Kim, Jeonbuk (KR); Ye Rang Kim, Jeonbuk (KR)

(73) Assignee: Industrial Cooperation Foundation Chonbuk National University, Jeonju-Su (KR)

( * ) Notice: Subject to any disclaimer, the term of this patent is extended or adjusted under 35 U.S.C. 154(b) by 74 days.

(21) Appl. No.: 13/500,326

(22) PCT Filed: Feb. 1, 2012

(86) PCT No.: PCT/KR2012/000791
§ 371 (c)(1),
(2), (4) Date: Aug. 3, 2012

(87) PCT Pub. No.: WO2012/105815
PCT Pub. Date: Aug. 9, 2012

(65) Prior Publication Data
US 2012/0288487 A1    Nov. 15, 2012

(30) Foreign Application Priority Data

Feb. 1, 2011  (KR) .................. 10-2011-0010268

(51) Int. Cl.
| | | |
|---|---|---|
| *A61K 47/34* | (2006.01) | |
| *C08L 79/04* | (2006.01) | |
| *C08G 63/685* | (2006.01) | |
| *A61K 9/16* | (2006.01) | |
| *C08J 3/12* | (2006.01) | |
| *C08J 3/14* | (2006.01) | |
| *A61P 11/00* | (2006.01) | |
| *A61K 31/522* | (2006.01) | |
| *A61P 1/16* | (2006.01) | |
| *C08G 73/06* | (2006.01) | |
| *A61K 38/44* | (2006.01) | |
| *A61K 38/00* | (2006.01) | |

(52) U.S. Cl.
CPC .......... *C08G 63/6856* (2013.01); *A61K 9/1641* (2013.01); *C08G 73/0633* (2013.01); *C08J 3/12* (2013.01); *C08J 3/14* (2013.01); *C08J 2367/02* (2013.01)
USPC ............. 424/94.4; 514/228.8; 514/772.7; 428/402; 435/325; 435/370; 525/58; 528/289

(58) Field of Classification Search
None
See application file for complete search history.

(56) References Cited

U.S. PATENT DOCUMENTS

2008/0033027 A1*  2/2008  Bascomb et al. ............. 514/411

OTHER PUBLICATIONS

Kim, Se.; Seong, K; Kim, O; Kim, So.; Seo, H; Lee, M; Khang, G; Lee, D "Polyoxalate Nanoparticles as a Biodegradable and Biocompatible Drug Delivery Vehicle" Biomacromolecules, 2010, 11(3), pp. 555-560.*
Seong, K; Seo, H; Ahn, W; Yoo, D; Cho, S; Khang, G; Lee, D "Enhanced Cytosolic Drug Delivery Using Fully Biodegradable Poly(mino oxalate) Particles" J. Controlled Release, Mar. 1, 2011, 152, pp. 257-263.*
Kim, Hyungmin; Kim, Yerang; Guk, Kyeonghye; Yoo, Donghyuck; Lim, Hyungsuk; Kang, Gilson; Lee, Dongwon "Fully Biodegradable and Cationic Poly(amino oxalate) Particles for the Treatment of Acetaminophen-induced Acute Liver Failure" Int. J. Pharm., Sep. 15, 2012 (published online Jun. 2, 2012), 434(1-2), pp. 243-250.*
Paramonov, Sergey E. et al. (Mar. 29, 2008) Fully Acid-Degradable Biocompatible Polyacetal Microparticles for Drug Delivery. Bioconjugate Chem. 2008, 19, 911-919.
Kim, Hyun Ah, et al. (Jul. 6, 2011) Combined delivery of dexamethasone and plasmid DNA in an animal model of LPS-induced acute lung injury. Journal of Controlled Release 156 (2011) 60-69.
Oh, Yu Jin, et al. (Nov. 9, 2010) Preparation of budesonide-loaded porous PLGA microparticles and their therapeutic efficacy in a murine asthma model. Journal of Controlled Release 150 (2011) 56-62.
Lee, Sungmun, et al. (Dec. 19, 2006) Polyketal Microparticles: A New Delivery Vehicle for Superoxide Dismutase. Bionconjugate Chem. 2007, 18, 4-7.

* cited by examiner

*Primary Examiner* — Jon P Weber
*Assistant Examiner* — Aaron J Kosar
(74) *Attorney, Agent, or Firm* — Renner Kenner Greive Bobak Taylor & Weber

(57) ABSTRACT

The present invention relates to the preparation of poly(amino oxalate) (PAOX) using oxalyl chloride, 1,4-cyclohexanedimethanol, and piperazinediethanol, the preparation of biodegradable polymer particles using the PAOX, and the use of PAOX particles as a drug delivery vehicle. The PAOX according to the present invention is a polymer that has three characteristics of biodegradability, biocompatibility, and cationic properties at the same time with appropriate hydrophobicity and thus can be prepared as particles that allow rapid drug release. Moreover, the particles improve the delivery efficiency of a drug into cells and thus can be efficiently used as a drug delivery vehicle for the treatment of acute inflammatory diseases such as acute liver failure and acute lung injury.

12 Claims, 12 Drawing Sheets

BIODEGRADABLE PAOX POLYMER PARTICLE WITH CATIONIC PROPERTY

TECHNICAL FIELD

The present invention relates to the preparation of poly (amino oxalate) (PAOX) using oxalyl chloride, 1,4-cyclohexanedimethanol, and piperazinediethanol, the preparation of biodegradable polymer particles using the PAOX, and the use of PAOX particles as a drug delivery vehicle.

BACKGROUND ART

Recent advances in biotechnologies have led to the discovery of new protein drugs available for the treatment of various diseases. Moreover, extensive research on cellular mechanisms of these proteins has continued to progress, and thus the treatment of diseases, which have been considered very difficult to treat, has been possible. While the value of proteins as therapeutic drugs has already been recognized for a long time, a large amount of proteins are required to obtain therapeutic effects due to short half-life and instability in vivo. Furthermore, protein-based drugs are made of peptide bonds and have ionic nature under a constant pH, and protein molecules tend to aggregate or absorb each other i.e., tend to adhere to each other. Accordingly, the protein molecules are easily denatured, and the denatured proteins lose their original functions.

In order to overcome these problems, various methods of binding proteins to biodegradable polymers through covalent bonds, adsorbing protein drugs on the surface of biodegradable polymer particles, or encapsulating protein drugs in biodegradable polymer particles have been developed.

So far, a method of preparing particles using biodegradable polymers such as poly(lactide-co-glycolide) (PLGA) or poly (lactic acid) (PLA) has been widely used as one of the methods for effective delivery of proteins. Among various biodegradable polymers, the PLGA is an US FDA-approved polymer and has been extensively utilized for medical applications including microspheres, sutures, implantable screws, pins and tissue engineering scaffolds. PLGA particles have achieved a certain degree of success for the delivery of proteins and vaccines to the immune system or to the systemic circulation. Furthermore, several PLGA-based particles loaded with therapeutic drugs are available on the market. An example of particles may include leuprolide (Lupron Depot) or triptorelin (Trelstar).

However, it has been reported that the initial release of proteins as macromolecules from hydrophobic polyester microparticles such as PLGA occurs primarily through pore diffusion in non-crystalline regions and the release rate is usually very slow. Slow release of therapeutic drugs from the PLGA microparticles may not be suitable for the treatment of acute inflammatory diseases such as acute liver failure and acute lung injury. To this end, a method of blending hydrophobic PLGA with hydrophilic polymers has been used to modify the hydration rate of the polymeric matrix. In addition, the PLGA produces acidic by-products after biodegradation, which may lower the surrounding pH and cause inflammation. Therefore, there is a great need to develop biodegradable polymer particles with excellent biocompatibility.

DISCLOSURE

Technical Problem

Accordingly, the present invention has been made to solve the above-described problems, and an object of the present invention is to provide poly(amino oxalate) (PAOX) prepared from a one-step reaction of oxalyl chloride, 1,4-cyclohexanedimethanol, and piperazinediethanol.

Moreover, another object of the present invention is to provide a drug delivery vehicle in which a drug is loaded in PAOX particles.

Technical Solution

To accomplish the above objects of the present invention, the present invention provides poly(amino oxalate) (PAOX) having the structure of formula 1:

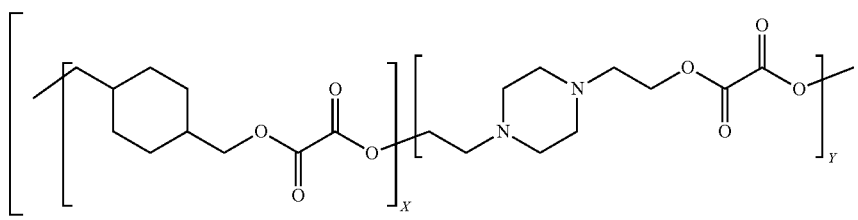

[Formula 1]

wherein n is an integer of 18 to 70, and the molar ratio of X to Y is 80 to 95:20 to 5.

Moreover, the present invention provides a method of preparing PAOX represented by the above formula 1 by polymerizing 1,4-cyclohexanedimethanol, oxalyl chloride, and piperazinediethanol.

The molar ratio of 1,4-cyclohexanedimethanol to piperazinediethanol may preferably be 80 to 95:20 to 5.

Furthermore, the present invention provides PAOX particles prepared by adding an emulsifier to PAOX represented by the above formula 1 followed by sonication and homogenization.

The emulsifier may comprise poly(vinyl alcohol).

The particles may preferably have an average size of 100 nm to 10 μm.

In addition, the present invention provides a drug delivery vehicle in which a drug is loaded in the particles.

The drug may comprise at least one selected from the group consisting of protein, compound, nucleic acid, and extract.

Advantageous Effects

The PAOX according to the present invention is a polymer that has three characteristics of biodegradability, biocompatibility, and cationic properties at the same time with appropriate hydrophobicity and thus can be prepared as particles that allow rapid drug release. Moreover, the particles improve the delivery efficiency of a drug into cells and thus can be efficiently used as a drug delivery vehicle for the treatment of acute inflammatory diseases such as acute liver failure and acute lung injury.

MODE FOR INVENTION

Figure 1:
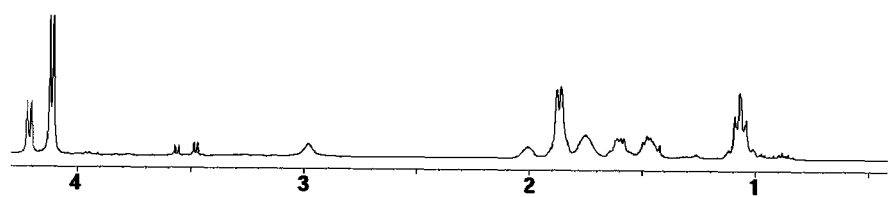
FIG. 1 is a diagram showing the $^1$H-NMR spectrum of PAOX in $D_2O$.

The present invention provides biodegradable poly(amino oxalate) (PAOX) with cationic properties having the structure of formula 1:

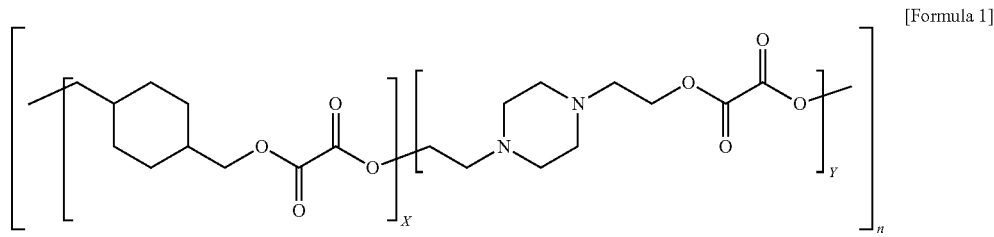

[Formula 1]

wherein n is an integer of 18 to 70, and the molar ratio of X to Y is 80 to 95:20 to 5.

Poly(amino oxalate) (PAOX) is a biodegradable polymer with cationic properties and has high hydrolysis rate. Despite the high hydrolysis rate, the PAOX maintains appropriate hydrophobicity and thus can exhibit significant stability in the preparation of particles using a single or double emulsion method.

Moreover, the present invention provides a method of preparing PAOX represented by the above formula 1 by polymerizing 1,4-cyclohexanedimethanol, oxalyl chloride, and piperazinediethanol.

The 1,4-cyclohexanedimethanol of the present invention has been used as a main component of the copolymer due to its excellent biocompatibility. Moreover, the 1,4-cyclohexanedimethanol has been approved as an indirect food additive that can be ingested by human beings. Furthermore, the 1,4-cyclohexanedimethanol has excellent cytotoxicity profiles ($LD_{50}$: 3,200 mg/kg oral intake) and can be rapidly removed from the body without undergoing significant enzymatic degradation in vivo.

The present invention relates to the preparation of biodegradable polymer poly(amino oxalate) (PAOX) with cationic properties using piperazinediethanol having amine groups as a monomer. Tertiary amine groups in piperazinediethanol can increase the hydrophilicity and cationic properties to accelerate the hydrolysis rate, compared to existing polyoxalate prepared by polymerizing 1,4-cyclohexanedimethanol and oxalyl chloride only. In one embodiment of the present invention, the hydrolysis kinetics of PAOX was determined by measuring the decrease in molecular weight due to the hydrolysis at pH 5.5 and pH 7.4 while maintaining the temperature of 37° C. As a result, the hydrolysis half-life of PAOX was about 36 hours at pH 7.4 and about 14 hours at pH 5.5.

The PAOX may be prepared by varying the ratio of 1,4-cyclohexanedimethanol to piperazinediethanol based on 100% oxalyl chloride. In terms of stability, the molar ratio of 1,4-cyclohexanedimethanol to piperazinediethanol may preferably be 80 to 95:20 to 5 for the preparation of particles. More preferably, the molar ratio may be 85:15.

Moreover, the present invention provides PAOX particles prepared by adding an emulsifier to the PAOX followed by sonication and homogenization.

In more detail, the PAOX particles may be prepared by adding the PAOX represented by the above formula 1 and dissolved in DCM to an emulsifier solution. The emulsifier may preferably be, but not limited to, poly(vinyl alcohol).

The particles may be prepared by an oil-in-water single emulsion method. In more detail, an oil/water emulsion is prepared by adding a drug to a PAOX polymer solution and adding an emulsifier solution thereto, followed by sonication. An emulsifier solution is added to the emulsion and then homogenized. After removing the remaining solvent using a rotary evaporator, the particles may be obtained by a centrifuge. The average size of the PAOX particles obtained through the above process may be 100 nm to 1,000 nm.

Moreover, the particles may be prepared by a water/oil/water double emulsion method. In more detail, a water/oil emulsion is prepared by adding a drug to a PAOX polymer solution followed by sonication and homogenization, and a water/oil/water emulsion is then prepared by adding the water/oil emulsion to an emulsifier solution followed by sonication and homogenization. The particles may be obtained after removing the solvent using a rotary evaporator. The average size of the PAOX particles obtained through the above process may be 1 to 10 μm, preferably about 2 μm.

When the drug included in the PAOX particles is a soluble macromolecule such as protein, peptide, nucleic acid, etc., the PAOX particles may preferably be prepared by the water/oil/water double emulsion method, whereas, when the drug included in the particles is an insoluble compound, the PAOX particles may preferably be prepared by the oil-in-water single emulsion method.

The PAOX particles have cationic properties and can allow rapid drug release due to the presence of amine groups. Moreover, the drug can escape from endosomes to the cytoplasm due to proton sponge effects, which enhances the efficiency of intracellular drug delivery. That is, it could be seen that the tertiary amines in piperazinediethanol increases the hydrophilicity and cationic properties and further improve the efficiency of intracellular drug delivery, compared to existing polyoxalate. In one embodiment of the present invention, it was confirmed by cell experiments that PAOX particles loaded with a cell membrane impermeable fluorescent calcein of the present invention helped the escape of calcein from endosomes. Moreover, in another embodiment of the present invention, it was confirmed that PAOX particles loaded with catalase, a material that inhibits the generation of hydrogen peroxide, showed the higher inhibitory effects on the generation of hydrogen peroxide in lipopolysaccharide-stimulated macrophages, in comparison with catalase-loaded PLGA particles. In still another embodiment of the present invention, it was confirmed that pentoxifylline-loaded PAOX particles had excellent drug delivery capability in animal models of acute liver failure induced by acetaminophen (APAP).

Moreover, the present invention provides a drug delivery vehicle in which a drug is loaded in the PAOX particles.

In the present invention, the term "drug delivery vehicle" means a drug carrier that can control the continuous release of a drug for a long time. One or more drugs may be encapsulated in the drug delivery vehicle of the present invention, and the degradation rate can be freely controlled depending on the type of the drug and the purpose of administration. Furthermore, the drug delivery vehicle can provide effective control of drug release. It is possible to effectively control and improve the characteristics of the delivery vehicle by evaluating and comparing the drug encapsulation rate, physicochemical properties, efficacy and stability of the prepared drug delivery vehicle, the degradation rate of the polymeric matrix, the performance data depending on shape conditions, etc. The drug loaded in the drug delivery vehicle of the present invention may be released by the diffusion, dissolution, osmotic pressure, ion exchange, etc.

The drug that can be carried by the drug delivery vehicle includes all biological and chemical materials used for the prevention, treatment, or alleviation of diseases. In more detail, the drug includes, but not limited to, various types such as protein, peptide, compound, extract, nucleic acid (DNA, RNA, oligonucleotides, and vectors), etc. The drug that can be used in the present invention is not limited by specific drugs or classifications and includes, for example, antioxidants, antibiotics, anticancer drugs, anti-inflammatory analgesic drugs, anti-inflammatory drugs, antiviral drugs, antimicrobial drugs, hormones, etc. The drug may be mixed with various excipients such as diluents, release retardants, inert oil, binders, etc. used in the art. An example of the protein drug may include, but not limited to, superoxide, catalase, glutathione, etc. Moreover, an example of the compound drug may include, but not limited to, pentoxifylline, dexamethasone, ibuprofen, naproxen, indomethacin, celecoxib, piroxicam, diclofenac, tocopherol, tocotrienol, resveratrol, ascorbic acid, lycopene, naringenin, etc.

The drug delivery vehicle of the present invention may include a pharmaceutically acceptable carrier and can be administered by any appropriate method. The drug delivery vehicle of the present invention may be formulated into various forms such as oral formulations, sterile injection solutions, etc. by any typical method. Moreover, the drug delivery vehicle may be prepared as solid particle powder and thus can also be used as an inhalable drug delivery vehicle.

Diseases in which the drug delivery vehicle of the present invention can be used may include, but not limited to, acute inflammatory diseases such as acute liver failure, acute lung injury, etc.

Next, the present invention will be described in detail with reference to Examples. The following Examples are intended to merely illustrate the present invention, and the scope of the present invention is not limited thereby.

EXAMPLE 1

Materials and Methods

1. Synthesis of PAOX Polymer 1,4-Cyclohexanedimethanol (13.34 mmol) and piperazinediethanol (2.35 mmol) were dissolved in 30 mL of dry dichloromethane (DCM), under nitrogen, to which pyridine (37.0 mmol) was added dropwise at 4° C. Oxalyl chloride (15.7 mmol) in 5 mL of dry DCM was added dropwise to the mixture at 4° C. The reaction was kept under nitrogen atmosphere at room temperature for 6 hours, quenched with a brine solution, and extracted from layer separation caused by the addition of additional DCM. The combined organic layers were dried over anhydrous $Na_2SO_4$ and concentrated under vacuum. The obtained polymer was isolated by the precipitation in cold hexane (yield >70%). The molecular weight was determined by a gel permeation chromatography (GPC, Futecs, Korea) using polystyrene standards. The chemical structure of polymers was identified with a 400 MHz $^1H$ NMR spectrometer (JNM-EX400, JEOL). ($^1H$ NMR in deuterated chloroform on a 400 MHz spectrometer: 4.1-4.5 (m, $CH_2$—OCO), 2.9-3.0 (m, $NCH_2CH_2NCH_2CH_2$), 1.8-2.0 (m, $CH_2CH$), 1.4-1.6 (m, $CH_2CH_2CHCH_2CH_2CH$), 1.0-1.1 (m, $CH_2CH_2CHCH_2CH_2CH$)).

2. Preparation and Characterization of PAOX Particles

Drug-loaded PAOX particles were prepared by a water/oil/water double emulsion method. 10 mg of proteins (BSA-FITC or catalase) in 100 mL of deionized water were added into 1 mL of DCM containing 150 mg of PAOX, followed by sonication (Fisher Scientific, Sonic Dismembrator 500) for 30 seconds and homogenization (PRO Scientific, PRO 200) for 1 minute. The prepared w/o emulsion was added into 10 mL of 8% (w/w) aqueous poly(vinyl alcohol) (PVA) solution and the mixture was homogenized for 1 minute. The resulting w/o/w emulsion was stirred to evaporate the solvent for 3 hours at room temperature. PAOX particles were obtained by the centrifugation at 11,000×g for 5 minutes at 4° C. followed by lyophilization of the recovered pellets. ~45 mg of BSA-FITC was encapsulated in 1 mg of PAOX particles and the protein encapsulation efficiency was >70%. The drug encapsulation efficiency of PAOX particles may vary depending on the solubility of the drug and is not intended to limit the scope of the present invention.

Empty PAOX particles were prepared by an oil-in-water single emulsion method. 50 mg of PAOX polymers dissolved in 500 mL of DCM were added to 5 mL of 10 (w/v) % PVA solution. The mixture was sonicated for 30 seconds and homogenized for 1 minute to form a fine o/w emulsion. The emulsion was added into 20 mL of 1 (w/w) % PVA solution and homogenized for 1 minute. Then, PAOX particles were obtained by centrifugation and lyophilization. The SEM images of PAOX particles were made using a scanning electron microscope (S-3000N, Hitachi). The particle size of PAOX particle suspension in PBS was measured by dynamic light scattering and their zeta potentials were measured using a particle analyzer (ELS-8000, Photal Otsuka Electronics, Japan).

3. Hydrolysis Kinetics of PAOX

PAOX polymers were ground into fine powders and placed in PBS (phosphate buffer solution, pH 7.4, 100 mM) under gentle mechanical stirring at 37° C. The hydrolyzed polymers were collected at specific time points and lyophilized. Their molecular weights were measured using a GPC to estimate the hydrolysis rate.

4. Cytotoxicity of PAOX Particles

The cytotoxicity of PAOX particles was investigated using a 3-(4,5-dimethylthiazol-2-yl)-2,5-diphenyltetrazolium bromide (MTT) assay. RAW 264.7 macrophage cells were seeded at a density of $1 \times 10^6$ cells/well in a 24 well plate and incubated to reach ~90% confluency. Cells were treated with various amounts of particles (10 mg/mL to 100 mg/mL) and incubated for 1 or 2 days. Each well was given 100 mL of MTT solution and incubated for 4 hours. 200 μL of dimethyl sulfoxide was added to cells to dissolve the resulting formazan crystals. After 10 minutes of incubation, the absorbance at 570 nm was measured using a microplate reader (Thermolex, Molecular Device Co.). The cell viability was determined by comparing the absorbance of particles-treated cells to that of control cells.

5. Confocal Laser Scanning Microscopy

RAW 264.7 cells were treated with 100 μL of BSA-FITC-loaded PAOX particle suspension (1 mg/mL in PBS) for 30 minutes. Particles containing media were removed and cells were washed with fresh media twice. The process in which the PAOX particles were internalized into cells and BSA-FITC was delivered to the cytoplasm was observed using a confocal laser scanning microscope (Carl Zeiss, Inc.) after 2, 4 and 20 hours, respectively.

Moreover, in order to investigate the effect of PAOX particles on the stability of endosomes following empty PAOX particle uptake, calcein, a cell membrane-impermeable fluorescent was used as a tracer. Cells were treated with 30 μg of calcein for 30 minutes, and the media were replaced with fresh media. Then, cells were incubated with 100 μg of empty PAOX or POX particles for 30 minutes. Particles containing media were removed and cells were washed with fresh media. Fluorescent images were captured 1 and 3 hours after incubation.

6. BSA-FITC Release Kinetics 10 mg of BSA-FITC-loaded PAOX particles were placed in a test tube containing 5 mL of PBS (pH 7.4). The tube was continuously shaken and incubated at 37 C. The tube was centrifuged at 5000×g for 1 minute. A 2 mL aliquot of supernatant was taken and replaced with an equal volume of fresh PBS. The concentration of BSA-FITC in the supernatant was measured using a fluorospectrometer (Jasco, FP6000, Japan), and the release kinetics was determined by comparing the concentrations of BSA-FITC standard solutions.

7. Drug Delivery to Cells 7-1. Catalase

To investigate the ability of PAOX particles to deliver protein drugs, catalase was used as a model protein drug. RAW 264.7 cells ($1 \times 10^6$ cells) were pretreated with catalase, catalase-loaded PAOX particles, catalase-loaded PLGA particles or empty PAOX particles for 12 hours and then stimulated with 1 μg of PMA (phorbol-12-myristate-13-acetate) to induce the production of hydrogen peroxide. PMA was used to stimulate cells for the production of reactive oxygen species including hydrogen peroxide. Then, DCFH-DA (dichlorofluorescin-diacetate) was added to each well and incubated for 30 minutes. The efficacy of PAOX particles to deliver catalase to cells was evaluated by measuring the intensity of the fluorescence produced by DCFH-DA with a flow cytometry caliber (Becton Dickinson, US).

7-2. Pentoxifylline

Pentoxifylline was used as a model compound drug. First, 100 mg of PAOX and 10 mg of pentoxifylline were completely dissolved in 1 mL of dichloromethane. Pentoxifylline-loaded PAOX particles were then prepared by a single emulsion method using PVA 5% and PVA 1%. The pentoxifylline-loaded PLGA particles were used as the control groups.

8. Measurement of Biodistribution

In order to investigate the function of PAOX particles as a drug delivery vehicle, the biodistribution was measured. 100 mg of PAOX polymers and 5 mg of fluorescent rubrene were used. PAOX particles were prepared by a single emulsion method using PVA 5% and PVA 1%. 10 mg of the PAOX particles were dispersed in 1 mL of sterilized PBS, and 200 μL of the resulting solution was injected into mouse tail veins. To investigate the accurate biodistribution, the heart, lungs, liver, spleen, and kidney were extracted 2 hours after the injection and identified.

9. Evaluation of Drug Delivery Efficiency in Animal Models of Acute Liver Failure On the assumption that the PAOX polymers rapidly deliver drugs to the cytoplasm due to high hydrolysis rate and proton sponge effects, which leads to more rapid treatment, mouse models of acute liver failure (ALF) were used as experimental models, and pentoxifylline (PEN) was used as a drug model.

While there are various causes of acute liver failure, the recently discovered cause is an overdose of Tylenol (acetaminophen, APAP) as antipyretic-analgesics, which accounts for more than 50% of the causes of ALF in USA and Europe. Liver failure leads to the failure of each organ and, in severe cases, leads to death. Moreover, the pentoxifylline used as a model drug is a drug used in ischemic liver disease.

In order to investigate the cytotoxicity of PAOX-PEN particles prepared by the method as described in the above section 7, a tetrazolium-based colorimetric MTT assay was performed. Moreover, an alanine transaminase (ALT) assay, which is mainly used for evaluation of liver functions, was performed to evaluate the effect of PAOX-PEN particles in terms of the amount of drug loaded in PAOX-PEN particles and daily dosages.

6-week-old BALB/c female mice were used for the experiments and classified into each group. The PAOX-PEN particles were dispersed in 10 mg/mL (PBS), and each of 50 μL, 100 μL, and 200 μL of the resulting solution was injected into mouse tail veins. In the case of free PEN, the drug solution was administered with the calculation of dose and, only PBS was administered to the negative control groups. After 1 hour, 200 μL of APAP in a concentration of 25 mg/mL was injected intraperitoneally to induce acute liver failure. The mice were sacrificed 10 hours later, and blood was taken from the heart. The blood was incubated for an appropriate period of time, and then plasma in the upper layer was obtained by centrifugation, followed by the ALT assay. Moreover, the liver was extracted from each mouse, followed by hematoxylin-eosin (H&E) staining and TUNEL staining.

EXAMPLE 2

Results

1. Synthesis and Characterization of PAOX

PAOX was synthesized from a one step condensation reaction between oxalyl chloride and two diols, cyclohexanedimethanol and piperazinediethanol, as shown in the following scheme 1. The content of piperazinediethanol (15 mol %) in PAOX was chosen after consideration of the degradation kinetics and stability under aqueous conditions. The obtained polymer was pale yellow solid after drying under high vacuum. The following scheme 1 represents the synthesis reaction of cationic PAOX:

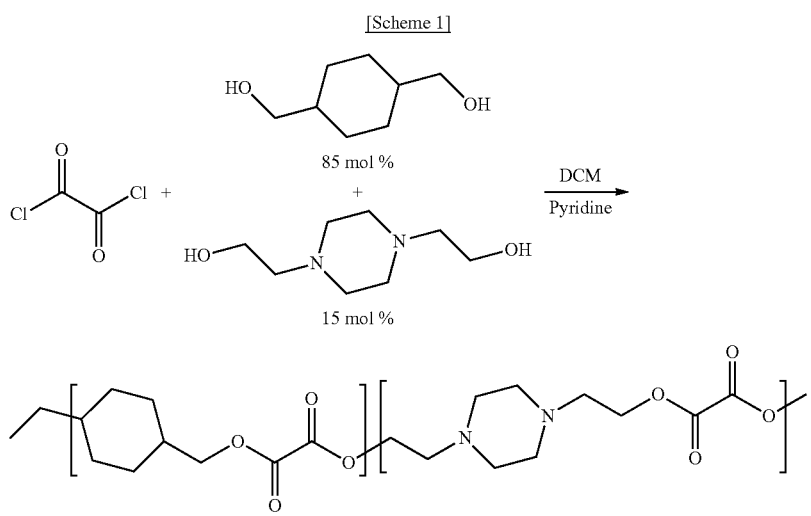

Figure 2:
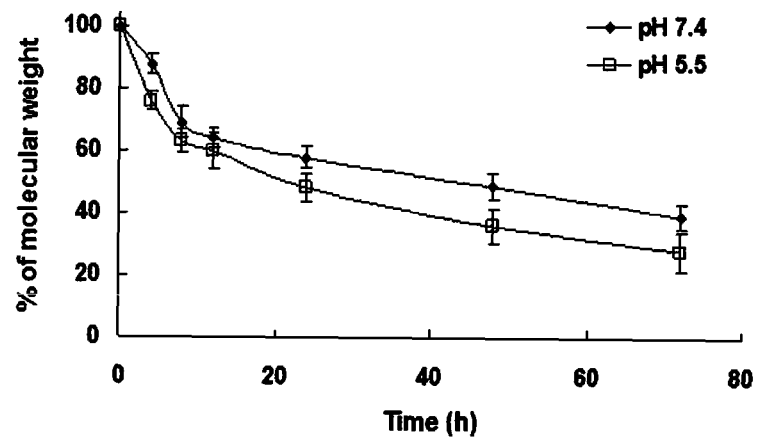
FIG. 2 is a graph showing the hydrolysis kinetics of PAOX (the numbers are the mean±standard deviation (n=3)).

The chemical structure of PAOX was confirmed by the $^1$H NMR (FIG. 1). 1,4-Cyclohexanedimethanol has methylene protons next to hydroxyl groups at 3.5 ppm, and methylene protons next to hydroxyl groups of piperazinediethanol appear at 3.6 ppm. The large peaks at ~4.2 ppm correspond to the methylene protons adjacent to peroxalate ester linkages, and protons of piperazine appeared at ~3.0 ppm, suggesting the successful polymerization of PAOX. The PAOX obtained from the above reaction had a molecular weight of ~12,000 with a polydispersity index of 1.8. The hydrolysis kinetics of PAOX was determined by measuring the molecular weight of finely ground PAOX after incubation in PBS at 37° C. at a pH of 5.5 and 7.4 to appropriate the pH of the environments within the endosomal vesicles and the cytoplasm, respectively. As shown in FIG. 2, the PAOX underwent faster hydrolytic degradation at pH 5.5 than pH 7.4 and the hydrolysis half-life of PAOX was ~36 hours at pH 7.4 and ~14 hours at pH 5.5.

2. Characterization of PAOX Particles

Figure 3:
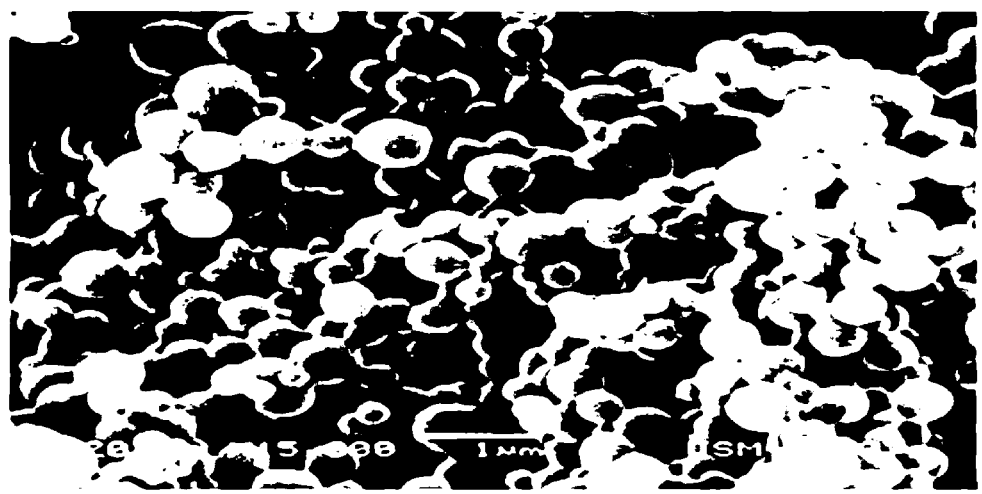
FIGS. 3 and 4 show SEM images of PAOX particles (empty PAOX particles (A); BSA-FITC-loaded particles (B).
Figure 4:
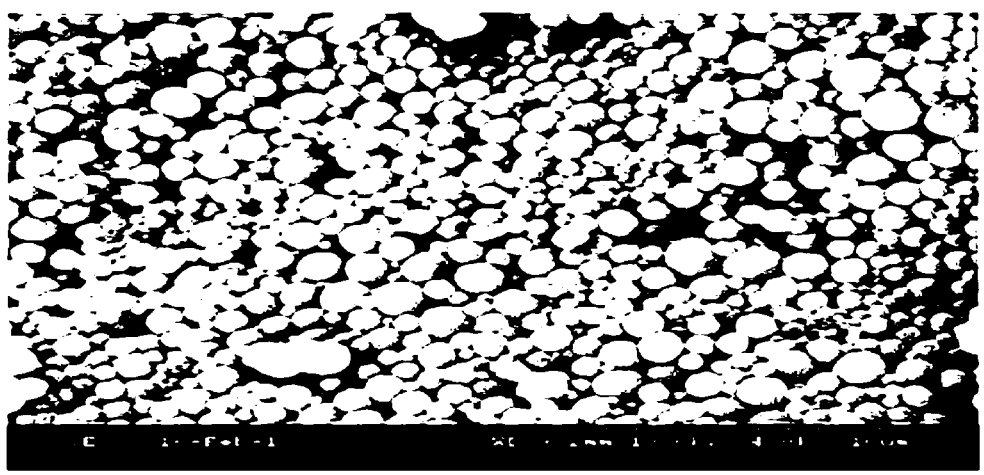
Figure 5:
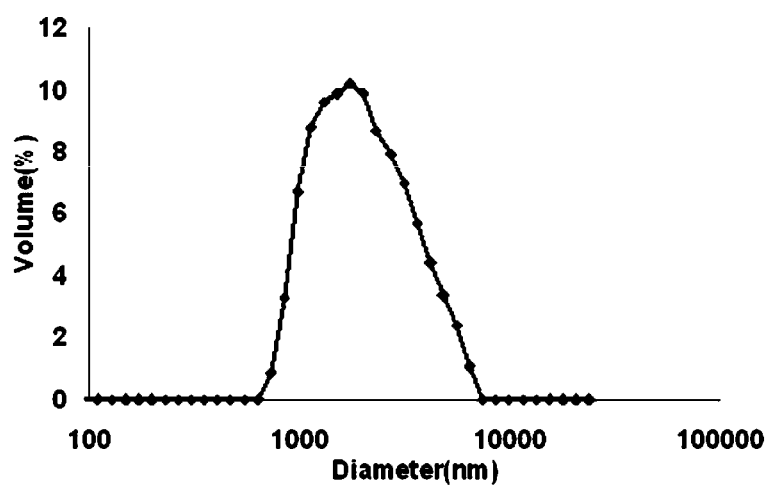
FIG. 5 is a graph showing the size of BSA-FITC-loaded PAOX particles measured by light scattering.

PAOX particles formulated by a single emulsion method were round spheres with smooth surface and an average diameter of ~450 nm (FIG. 3). Moreover, PAOX was formulated into particles by a double emulsion method with acceptable yields, >70%, which allowed proteins to be encapsulated in the particles. As shown in FIG. 4, BSA-FITC-loaded PAOX particles were spherical and polydispersed, with smooth surface. The BSA-FITC-loaded PAOX particles had an average diameter of ~1.7 μm (FIG. 5). Protein-loaded PAOX particles may be suitable for drug delivery applications, in particular, involving phagocytosis by macrophages.

Figure 6:
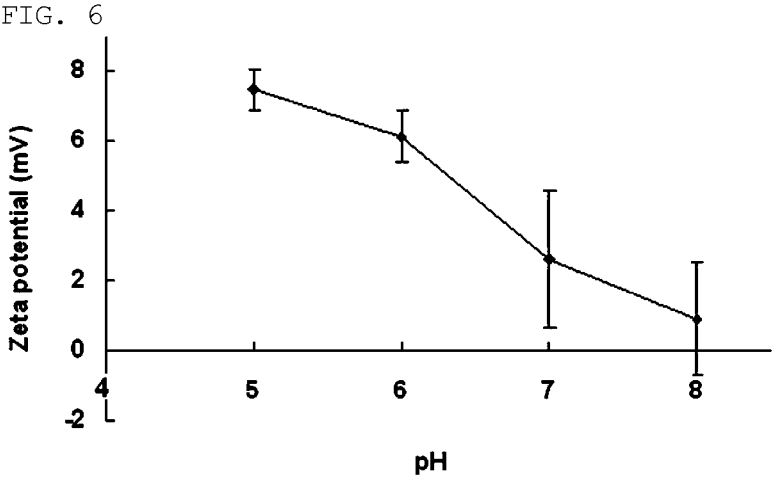
FIG. 6 is a graph showing the change in zeta potential of PAOX particles as a function of pH (the numbers are the mean±standard deviation (n=3)).
Figure 7:
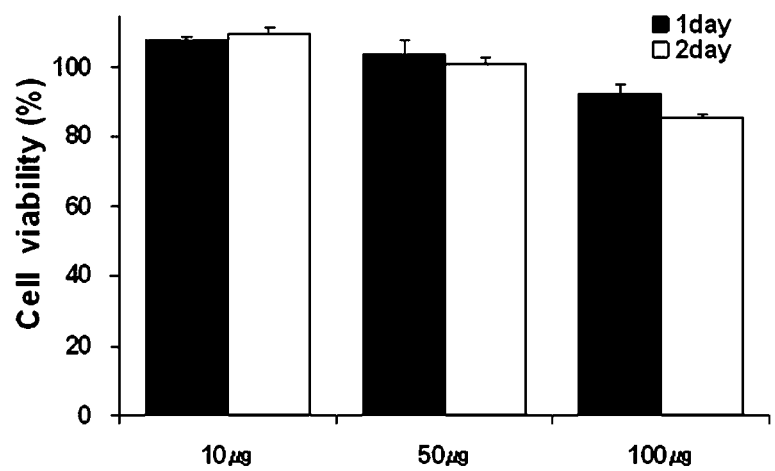
FIG. 7 is a graph identifying the cytotoxicity of PAOX particles by the MTT assay.

FIGS. 6 and 7 show the change in zeta potential of protein-loaded PAOX particles as a function of pH. The PAOX exhibited slightly positive charges at neutral pH and its zeta potential increased with decreasing pH. At an endosomal pH, the zeta potential of the particles was around+8 mV. The increased positive charge of PAOX may be due to the protonation of amino groups in piperazinediethanol.

The biocompatibility of PAOX particles was evaluated because one of great concerns for the design of drug delivery systems is their cytotoxicity. RAW 264.7 cells were incubated with various amounts of PAOX particles for 1 or 2 days and their viability was determined (FIG. 7). Slightly reduced cell viability was observed with cells treated with 100 μg of PAOX particles after 2 days. However, in general, the PAOX particles exhibited excellent cytotoxicity profiles for 2 days of observation. Therefore, the results demonstrate that the PAOX particles of the present invention have excellent biocompatibility and the incorporation of 15 mol % piperazinediethanol does not influence the biocompatibility.

3. In Vitro Drug Releases

Figure 8:
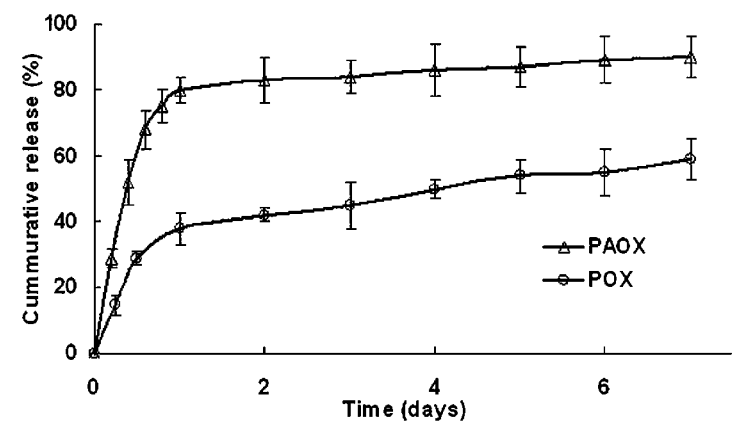
FIG. 8 is a graph showing the release kinetics of PAOX particles at pH 7.4 (the numbers are the mean±standard deviation (n=3)).

In order to determine whether the cationic PAOX particles of the present invention have suitable drug release profiles for the treatment of acute inflammatory diseases, the release kinetics of PAOX particles was investigated using BSA-FITC as a model protein (FIG. 8). The PAOX particles released BSA-FITC with an initial burst of about 80% over the first 24 hours. The initial burst release may be attributed to proteins that were loosely adsorbed on the surface or poorly entrapped in the particles. The initial burst was followed by slow and sustained release. The protein release kinetics of PAOX particles were compared with that of BSA-FITC-loaded POX particles. The POX and PAOX particles showed a similar protein release pattern, but the PAOX exhibited a faster protein release profile than POX. The faster protein release kinetics of PAOX particles is ascribed mainly to the tertiary amine groups in the backbone, which provide the polymer with hydrophilic nature and accelerate its degradation.

4. Cellular Uptake and Intracellular Delivery

Figure 9:
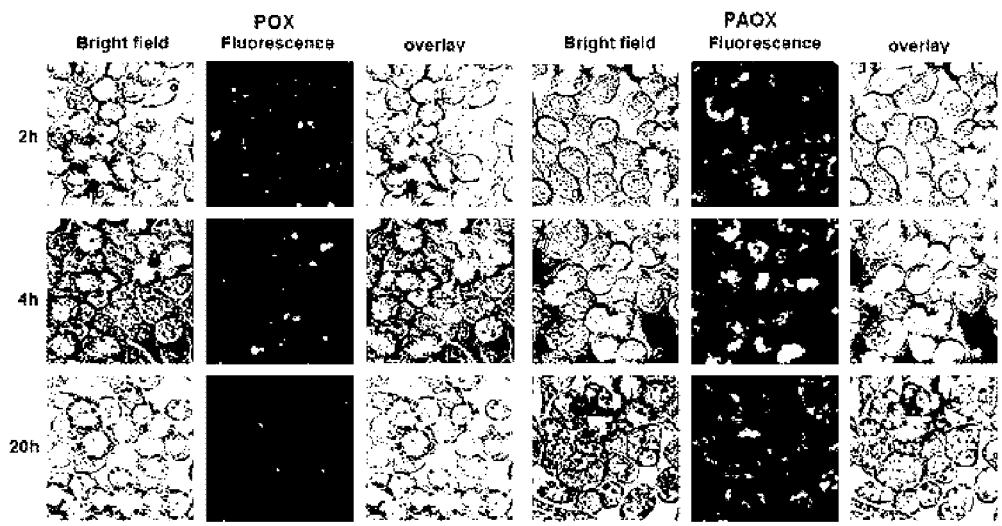
FIG. 9 shows confocal laser scanning micrographs of incubated cells treated with calcein.

In order to demonstrate whether the cationic properties of the PAOX of the present invention facilitates the cellular uptake or phagocytosis, the internalization of BSA-FITC-loaded PAOX particles was investigated using a confocal laser scanning microscope. FIG. 9 illustrates the fluorescence images of RAW 264.7 cells incubated with BSA-FITC-loaded PAOX particles or BSA-FITC-loaded POX particles at various time points. At 2 hours after incubation, green fluorescence was observed on the periphery of cells, indicating phagocytosis by cells and internalization in endosomes. The PAOX particles showed more green fluorescence than POX particles, suggesting the enhanced cellular uptake of PAOX particles. Green fluorescence became dispersed into the cytoplasm and its intensity increased with time, suggesting the escape of BSA-FITC from the PAOX particles to the cytoplasm. The FITC-BSA delivered by the POX particles became weak 20 hours after incubation, but much brighter green fluorescence was observed with the FITC-BSA delivered by the PAOX particles, indicating effective protection of proteins by the PAOX particles. These observations demonstrate that the presence of tertiary amine groups in PAOX results in the enhanced intracellular delivery of proteins by facilitating the cellular uptake and the endosomal escape of proteins.

Figure 10:
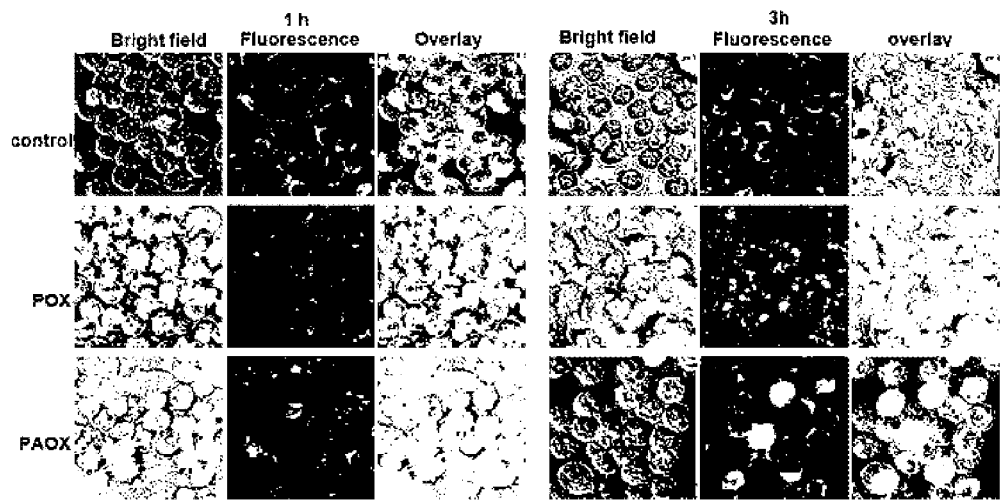
FIG. 10 shows confocal laser scanning micrographs of cells incubated with BSA-FITC-loaded POX particles or BSA-FITC-loaded PAOX particles.

In order to further confirm the effective escape of drugs delivered from endosomes by the cationic PAOX particles of the present invention, a cell membrane impermeable calcein was used and its distribution was visualized. As shown in FIG. 10, cells treated with calcein alone showed a punctuate distribution of fluorescence, indicating that calcein was internalized in the endosomes or endosomal compartments in the periphery of cells. However, after the treatment of POX particles, the internalized calcein diffused from the endosome, and green fluorescence was observed in the cytoplasm 3 hours after incubation. This indicates that the POX particles help the escape of calcein from endosomes to some extent. In contrast, the addition of PAOX particles induced much more calcein release from endosomes. Calcein diffused in the cytoplasm and its intensity increased 3 hours after the addition of PAOX particles. The results demonstrate that the cationic properties of the PAOX of the present invention would facilitate the endosomal escape of protein drugs to enhance the intracellular drug delivery.

5. Drug Delivery to Cells 5-1. Catalase Delivery

Figure 11:
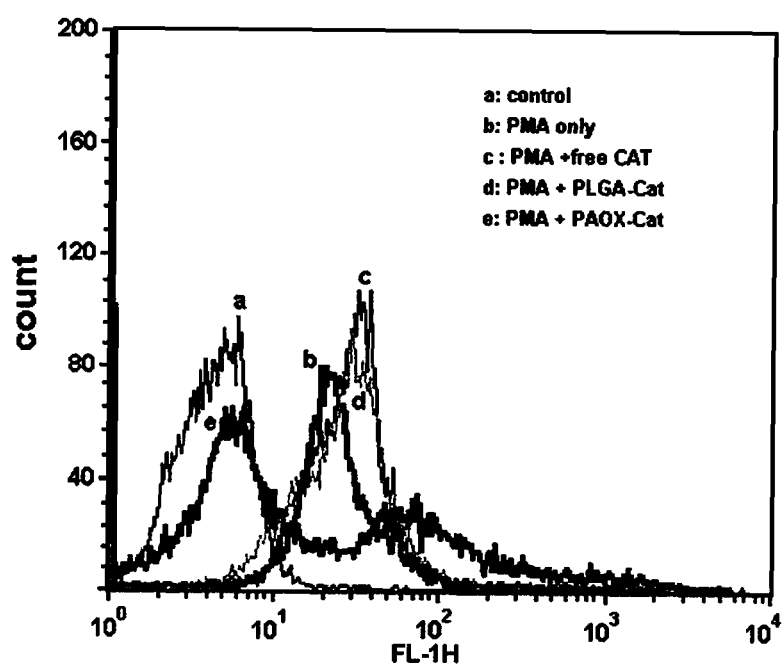
FIG. 11 is a graph showing enhanced delivery of catalase (CAT) from endosomes to the cytoplasm in RAW 264.7 macrophage cells by PAOX particles.

FIG. 11 illustrates the results of flow cytometry demonstrating the effects of catalase on the production of hydrogen peroxide in the PMA-stimulated cells. PMA-stimulated cells showed a strong fluorescence because DCFH-DA was oxidized by intracellular hydrogen peroxide. On the contrary, pretreatment with free catalase (CAT) or empty PAOX particles showed no inhibitory effects on the PMA-induced fluorescence. Catalase delivered by PLGA particles exhibited the slight inhibitory effects on PMA-induced fluorescence. However, pretreatment with 100 μg of catalase-loaded PAOX particles dramatically reduced the PMA-induced fluorescence, from which it was confirmed that the PAOX particles of the present invention has an excellent function as a protein drug delivery vehicle.

5-2. Pentoxifylline Delivery

Figure 12:
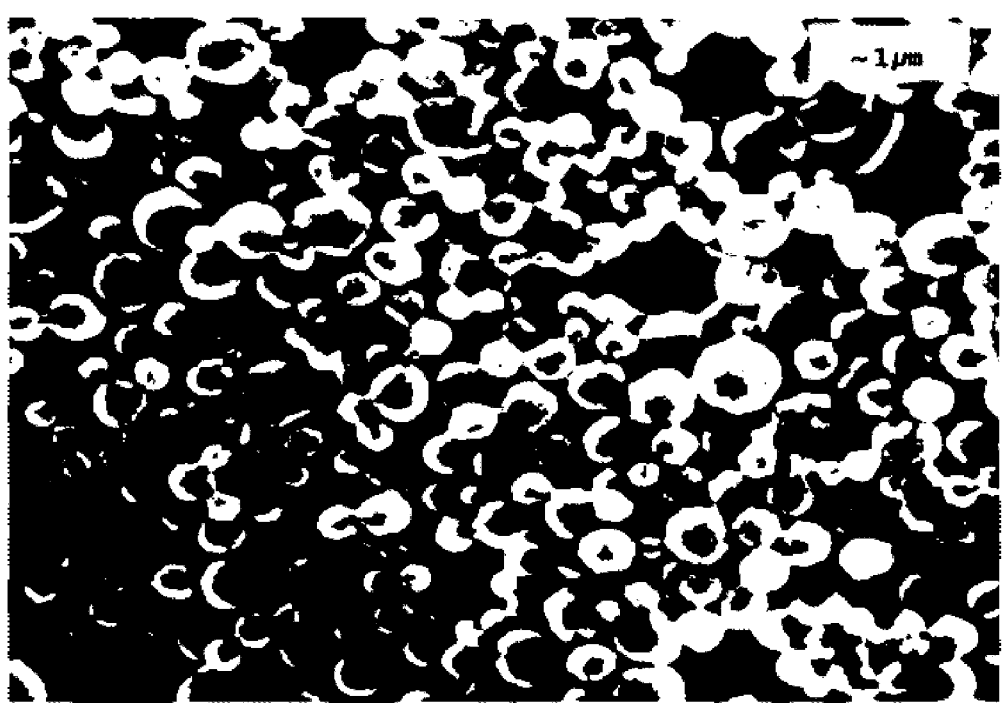
FIG. 12 shows an SEM image of the surface of PAOX-PEN particles.
Figure 13:
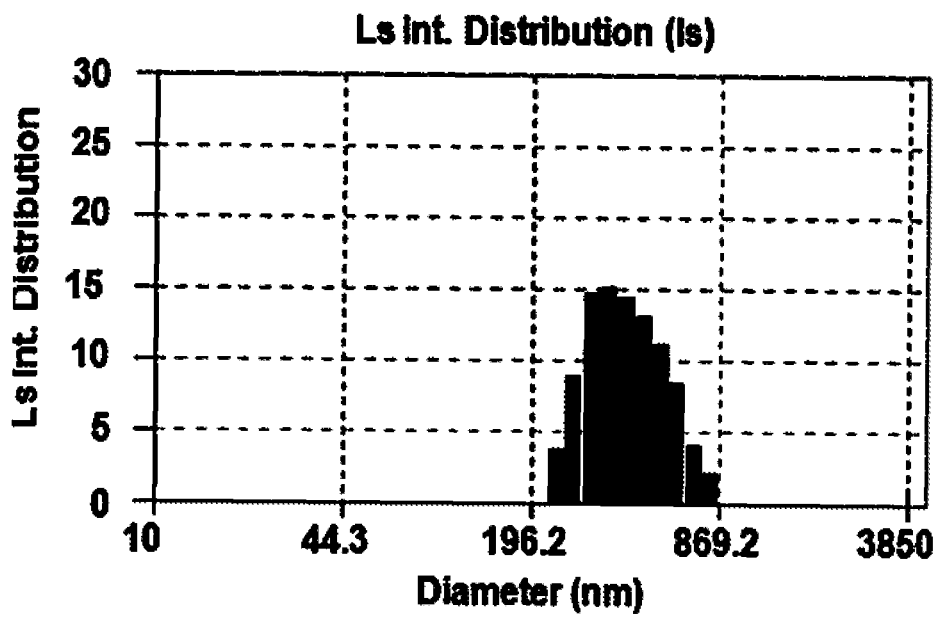
FIG. 13 is a graph showing the size of PAOX-PEN particles measured by light scattering.

FIGS. 12 and 13 illustrate the surface and size of pentoxifylline particles. FIG. 12 shows the surface of pentoxifylline-loaded PAOX particles observed by a scanning electron microscope, from which it can be confirmed that the pentoxifylline-loaded PAOX particles are round spheres with smooth surface and have a sub-micrometer size even with the naked eye. FIG. 13 shows the size of pentoxifylline-loaded PAOX particles measured by light scattering, from which it can be confirmed that the pentoxifylline-loaded PAOX particles have a particle size of about 100 nm to 1,000 nm.

Figure 14:
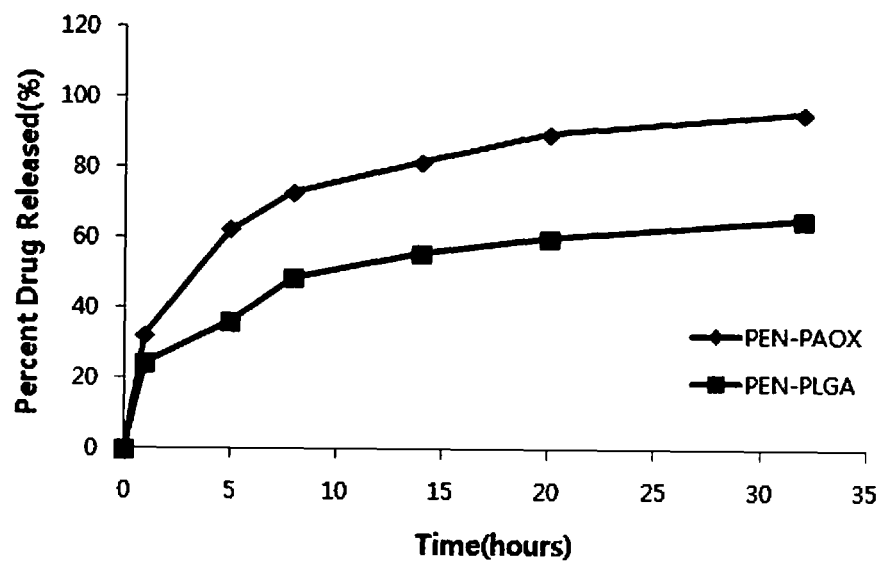
FIG. 14 is a graph showing the drug release rates of pentoxifylline-encapsulated PLGA and PAOX particles.

Moreover, as a result of the comparison of the drug release rates of pentoxifylline-encapsulated PLGA and PAOX particles, both PLGA and PAOX particles showed the initial burst behavior and had similar overall release behavior, but the PAOX particles exhibited a faster release rate than PLGA particles (FIG. 14), from which it was confirmed that the PAOX particles of the present invention has an excellent function as a drug delivery vehicle for diseases that require prompt treatment.

6. Measurement of Biodistribution

Figure 15:
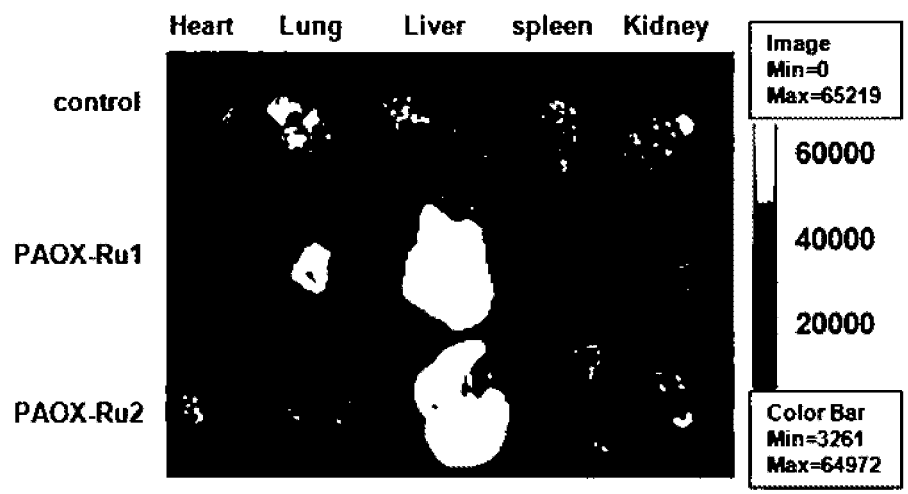
FIG. 15 shows the fluorescence intensity measured using an IVIS imaging system from each organ of mouse models to measure the biodistribution of fluorescent rubrene-encapsulated PAOX particles.

In order to investigate the biodistribution of PAOX particles, the extracted organs such as the heart, lungs, liver, spleen, and kidney were assigned to each experimental group (to each tissue), and then the fluorescence intensity was measured using an IVIS imaging system. As shown in FIG. 15, the liver exhibits the highest intensity, from which it can be seen that most PAOX particles were accumulated in the liver.

Figure 16:
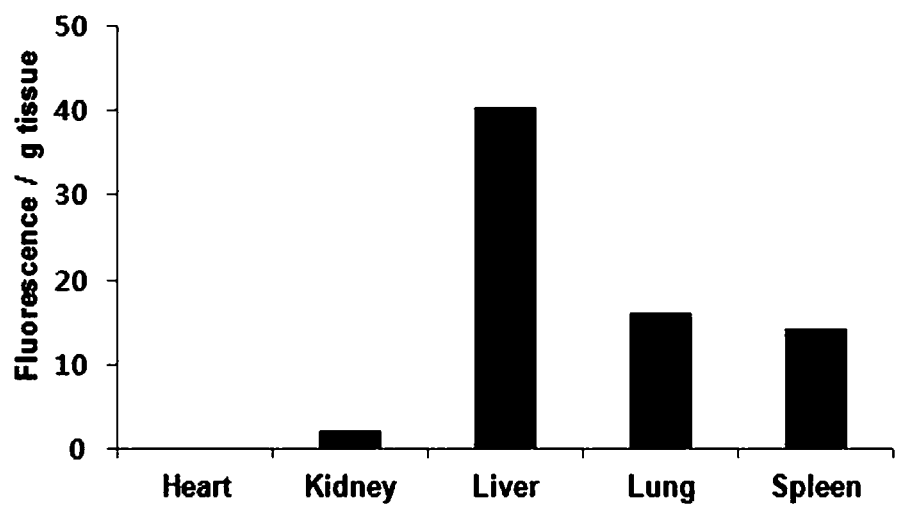
FIG. 16 is a graph showing the photoluminescence (PL) measured to quantify the fluorescence intensity of FIG. 15.

Moreover, the results of the fluorescence intensity were quantified by measuring the photoluminescence and confirmed by plotting a graph. After measuring the weight of each organ, the tissue of each organ was mixed with a solution of Triton-X 100 and PBS mixed in a ratio of 4:1 according to its weight and then homogenized. After centrifugation, the supernatant was separated to measure the photoluminescence (PL). As a result of the experiment, the liver exhibited the highest fluorescence value, and the lungs and spleen showed the next highest values as shown in FIG. 16. It was determined from the experiments that, as most of the PAOX particles were accumulated in the liver, when the PAOX particles of the present invention are applied to the delivery of drugs for the treatment of acute liver failure, the PAOX particles can exhibit high efficiency.

Figure 17:
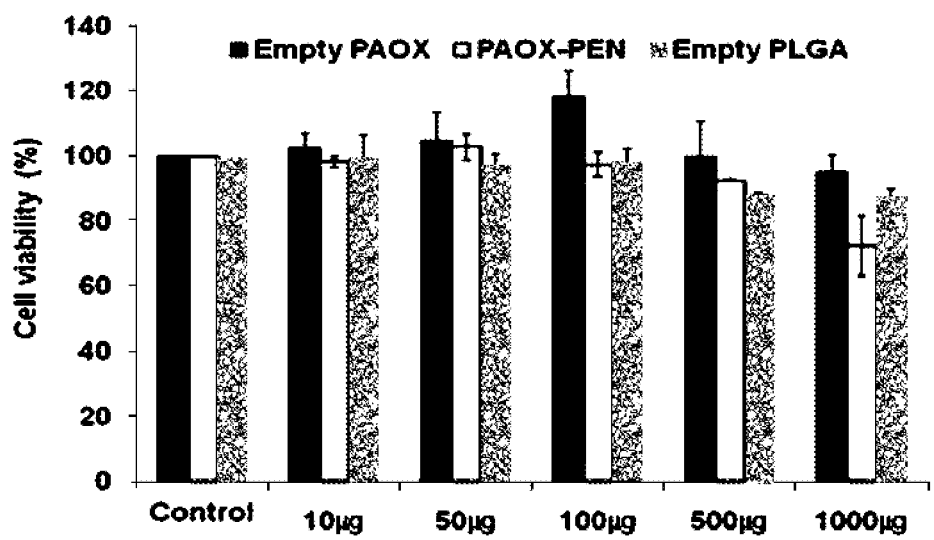
FIG. 17 is a graph identifying the cytotoxicity of PAOX-PEN particles by the MTT assay.

7. Evaluation of Drug Delivery Efficiency in Animal Models of Acute Liver Failure As a result of investigating the cytotoxicity of pentoxifylline-encapsulated PAOX (PAOX-PEN) particles, cell viability of about 80% was observed even when 1,000 μg of PAOX-PEN particles placed in a 24 well plate were incubated for 40 hours (FIG. 17). This is similar to the results of PLGA particles, which are conventionally used as a drug delivery vehicle, from which it was confirmed that the PAOX-PEN particles of the present invention have excellent intracellular and biological stability.

Figure 18:
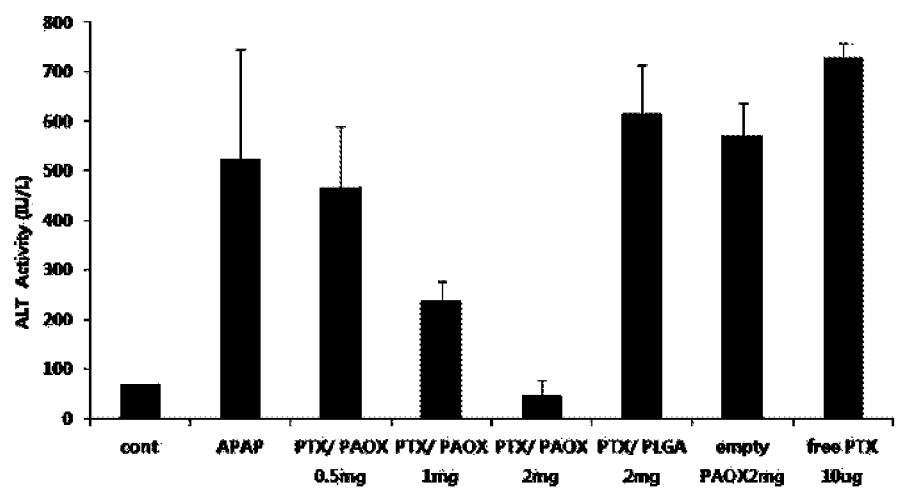
FIG. 18 is a graph showing the drug delivery system of PAOX-PEN particles identified from acute liver failure mouse models by the ALT assay.

Moreover, the ALT assay results to determine the therapeutic effect of PAOX-PEN particles are shown in FIG. 18. The group treated with 0.5 mg of PAOX-PEN particles showed a slight ALT reduction effect, but the group treated with 1 mg of PAOX-PEN particles showed a value which was about half of that of the group treated with APAP alone. Moreover, the group treated with 2 mg of PAOX-PEN particles was recovered to a similar level to that of the group treated with PBS alone. The groups treated with 10 ug of free PEN and 2 mg of PLGA-PEN particles, which correspond to the amount loaded in the group treated with 2 mg PAOX-PEN particles, showed no ALT reduction effects. It was determined that the above results were attributed to the passive liver-targeting capability, rapid degradation, and high release rate of the PAOX particles.

Figure 19:
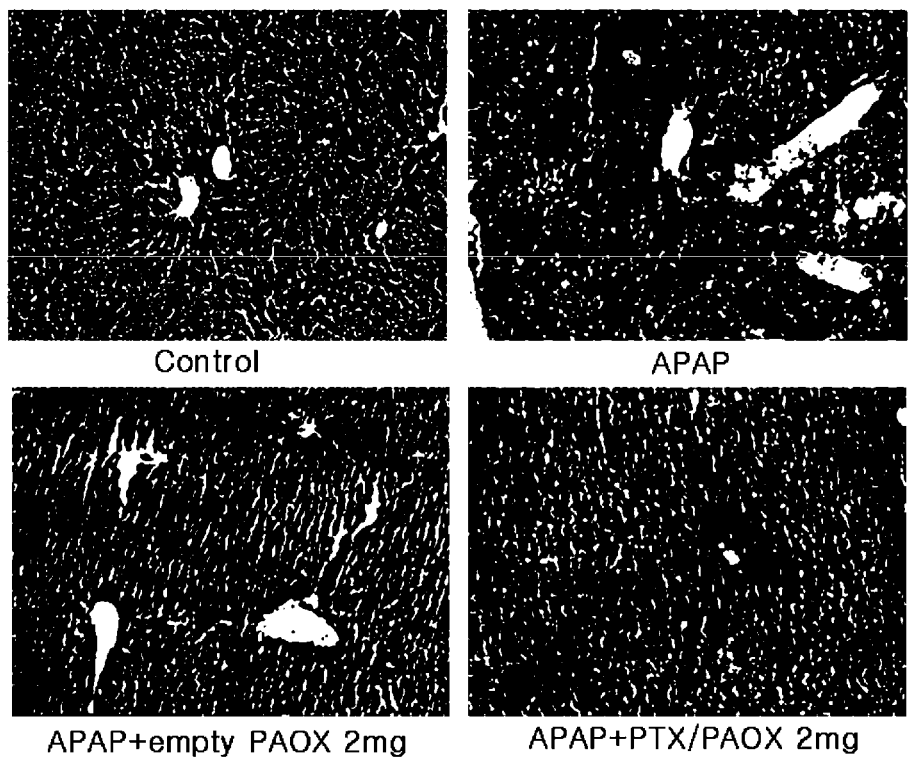
FIG. 19 shows the results of hematoxylin-eosin staining of liver tissues of acute liver failure mouse models.

Moreover, as a result of analyzing the images of hematoxylin-eosin (H&E) staining of the livers extracted from the experimental animals, it was confirmed that a large amount of inflammatory cells such as neutrophil migrated to the liver and the destruction and apoptosis of stellate and kupffer cells occurred in the group with liver failure caused by APAP (FIG. 19). However, it could be confirmed that the liver injury was significantly alleviated in the group treated with 2 mg of PAOX-PEN particles, and empty PAOX as the control group showed no effects.

Figure 20:
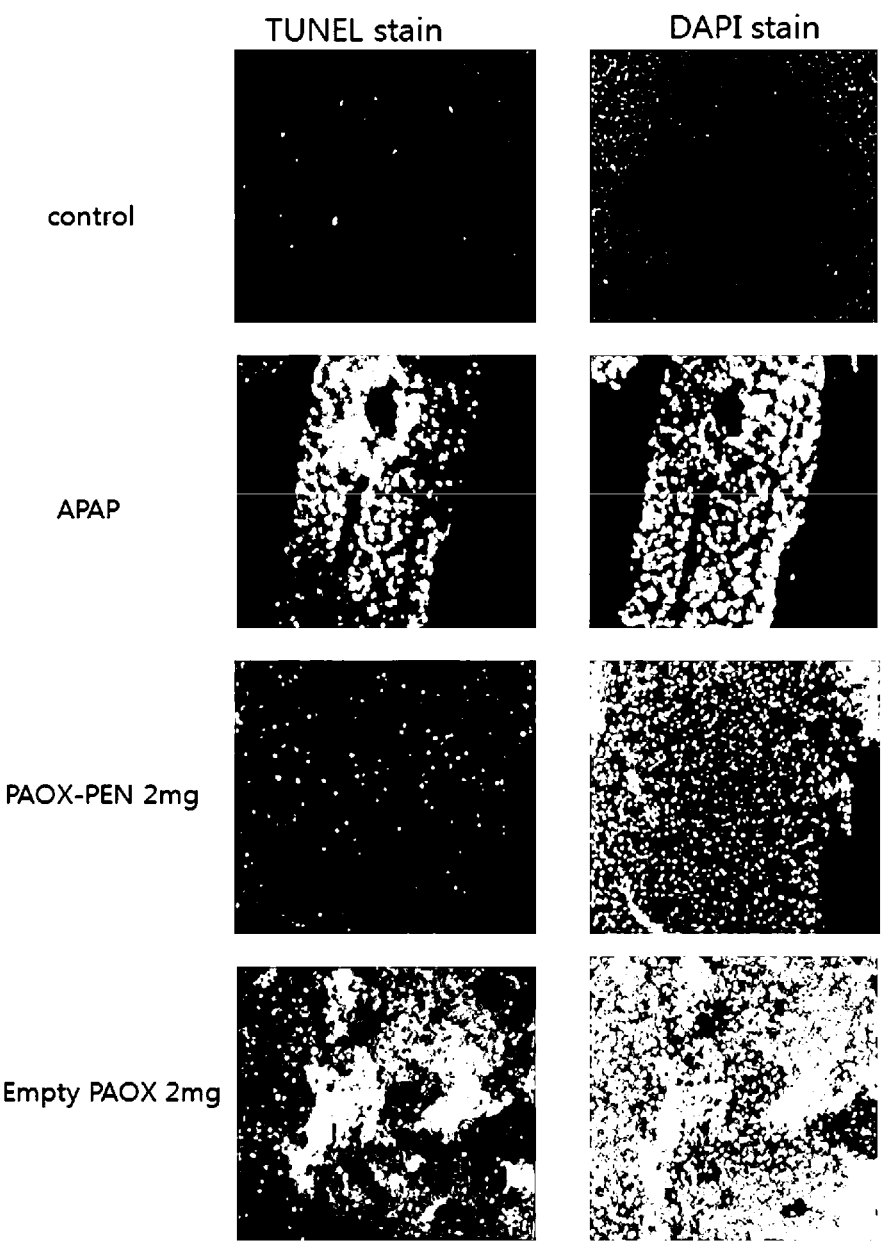
FIG. 20 shows the results of TUNEL staining of liver tissues of acute liver failure mouse models.

The above-described experimental results were confirmed again through TUNEL staining. As shown in FIG. 20, it was confirmed that the apoptosis of stellate and kupffer cells occurred in the group with liver failure caused by APAP and the apoptosis was inhibited in the group treated with 2 mg of PAOX-PEN particles.

It can be confirmed from the overall experimental results that the PAOX particles have excellent functions as a drug delivery vehicle.

INDUSTRIAL APPLICABILITY

The PAOX according to the present invention is a polymer that has three characteristics of biodegradability, biocompatibility, and cationic properties at the same time with appropriate hydrophobicity and thus can be prepared as particles that allow rapid drug release. Moreover, the particles improve the delivery efficiency of a drug into cells and thus can be efficiently used as a drug delivery vehicle for the treatment of acute inflammatory diseases such as acute liver failure and acute lung injury.

The invention claimed is:

1. A poly(amino oxalate) (PAOX) compound having the structure of formula (I):

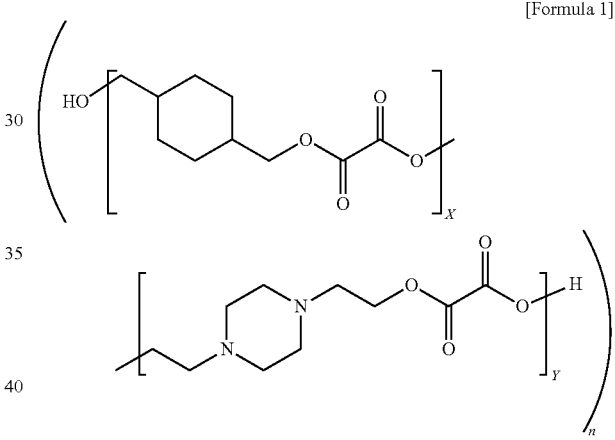

[Formula 1]

wherein n is an integer of 18 to 70, and the molar ratio of X:Y is 80:20 to 95:5.

2. A method of preparing the PAOX compound of claim 1, the method comprising:
polymerizing in a solution thereof 1,4-cyclohexanedimethanol, oxalyl chloride, and piperazinediethanol for a period of time and conditions sufficient to form said PAOX composition, said PAOX compound having the structure of formula (I),

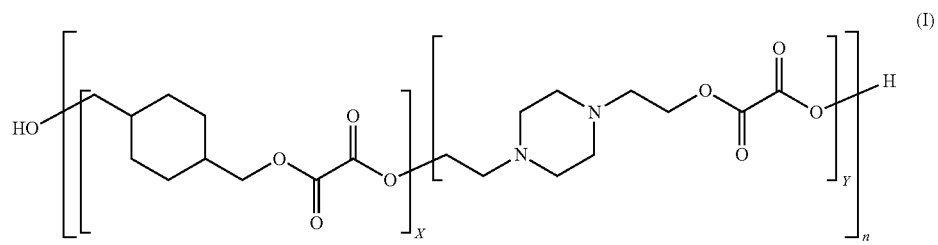

(I)

wherein n is an integer of 18 to 70, and the molar ratio of X:Y is 80:20 to 95:5; and recovering said PAOX compound from said solution.

3. The method of claim 2, wherein the molar ratio of 1,4-cyclohexanedimethanol to piperazinediethanol is 80:20 to 95:5.

4. A composition comprising particles that contain the PAOX compound of claim 1, the particles prepared by adding an emulsifier to the PAOX compound of claim 1 followed by sonication and homogenization thereof for a period of time and conditions sufficient to produce said composition comprising said PAOX compound-containing particles.

5. The composition of claim 4, wherein the emulsifier is poly(vinyl alcohol).

6. The composition of claim 4, wherein the particles have an average size of 100 nm to 10 μm.

7. A drug delivery vehicle comprising the composition of claim 4, wherein the particles are loaded with a drug.

8. The drug delivery vehicle of claim 7, wherein the drug comprises at least one deliverable material selected from the group consisting of protein and nucleic acid.

9. The drug delivery vehicle of claim 8, wherein the protein comprises at least one protein selected from the group consisting of catalase and superoxide dismutase (SOD).

10. The drug delivery vehicle of claim 7, wherein the compound comprises at least one drug selected from the group consisting of pentoxifylline, dexamethasone, ibuprofen, naproxen, indomethacin, celecoxib, piroxicam, diclofenac, tocopherol, tocotrienol, resveratrol, ascorbic acid, lycopene, and naringenin.

11. The drug delivery vehicle of claim 7, wherein the drug delivery vehicle is used for treating an acute inflammatory disease.

12. The drug delivery vehicle of claim 11, wherein the acute inflammatory disease is acute liver failure or acute lung injury.

* * * * *